US012766265B2

(12) United States Patent
Shanley et al.

(10) Patent No.: US 12,766,265 B2
(45) Date of Patent: Oct. 20, 2026

(54) SYSTEM AND METHOD FOR MULTIPLE SITE DISPENSING OR INJECTION

(71) Applicant: CREDENCE MEDSYSTEMS, INC., Menlo Park, CA (US)

(72) Inventors: Conor Edward Shanley, Emerald Hills, CA (US); Jeff Tillack, Foster City, CA (US); Alan E. Shluzas, San Carlos, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 581 days.

(21) Appl. No.: 18/222,579

(22) Filed: Jul. 17, 2023

(65) Prior Publication Data

US 2024/0017012 A1 Jan. 18, 2024

Related U.S. Application Data

(60) Provisional application No. 63/390,049, filed on Jul. 18, 2022.

(51) Int. Cl.
*A61M 5/315* (2006.01)
*A61M 5/31* (2006.01)

(52) U.S. Cl.
CPC ...... *A61M 5/31501* (2013.01); *A61M 5/3137* (2013.01); *A61M 2005/31508* (2013.01)

(58) Field of Classification Search
CPC .......... A61M 5/31526; A61M 5/31501; A61M 5/3137; A61M 5/31595; A61M 5/31536;
(Continued)

(56) References Cited

U.S. PATENT DOCUMENTS

2015/0025502 A1* 1/2015 Spenser ............ A61M 5/31595 604/506

FOREIGN PATENT DOCUMENTS

| | | |
|---|---|---|
| WO | WO 2013/114357 | 8/2013 |
| WO | WO 2014/190222 | 11/2014 |

OTHER PUBLICATIONS

PCT International Search Report and Written Opinion for International Appln. No. PCT/US2023/027867, Applicant Credence Medsystems, Inc., dated Dec. 8, 2023.

(Continued)

*Primary Examiner* — Michael J Tsai
*Assistant Examiner* — Justin L Zamory
(74) *Attorney, Agent, or Firm* — Vista IP Law Group, LLP

(57) ABSTRACT

A system for fluid delivery includes a syringe body having proximal and distal ends, a syringe interior, and a syringe flange at the proximal end thereof. The system further includes a finger flange coupled to the syringe flange. Moreover, the system includes a stopper member disposed in the syringe interior. In addition, the system includes a plunger member coupled to the stopper member and having a ratchet portion. The system also includes a push member disposed coaxially around at least a portion of the plunger member and operatively coupled thereto, the push member having an outer telescoping member disposed at a proximal end thereof. The system further includes an inner telescoping member disposed slidably and at least partially in the outer telescoping member and operatively couple thereto. Moreover, the system includes a thumbpad disposed coupled to a proximal end of the inner telescoping member.

10 Claims, 22 Drawing Sheets

(58) Field of Classification Search
CPC .......... A61M 5/31555; A61M 5/31556; A61M 5/3156; A61M 5/31568; A61M 5/31573; A61M 5/31578; A61M 5/3158; A61M 5/31591; A61M 5/31593; A61M 2005/31508
See application file for complete search history.

(56) References Cited

OTHER PUBLICATIONS

Reporting reply to R. 161(1) & 162 EPC Written Opinion, EP application No. 23754497.8, Applicant Credence Medsystems, Inc., dated Aug. 22, 2025.

* cited by examiner

SYSTEM AND METHOD FOR MULTIPLE SITE DISPENSING OR INJECTION

The present application claims priority to U.S. Provisional Patent Application Ser. No. 63/390,049, filed on Jul. 18, 2022 and entitled "SYSTEM AND METHOD FOR MULTIPLE SITE INJECTION." This application also includes subject matter similar to the subject matter described in the following co-owned U.S. patent applications: (1) Ser. No. 14/321,706, filed Jul. 1, 2014, and entitled "SAFETY SYRINGE", (2) Ser. No. 14/543,787, filed Nov. 17, 2014, and entitled "SYSTEM AND METHOD FOR DRUG DELIVERY WITH A SAFETY SYRINGE"; (3) Ser. No. 14/696,342, filed Apr. 24, 2015, and entitled "SYSTEM AND METHOD FOR SAFETY SYRINGE"; (4) Ser. No. 15/801,239, filed Nov. 1, 2017, and entitled "SYSTEM AND METHOD FOR SAFETY SYRINGE"; (5) Ser. No. 15/801,259, filed Nov. 1, 2017, and entitled "SYSTEM AND METHOD FOR SAFETY SYRINGE"; (6) Ser. No. 15/801,281, filed Nov. 1, 2017, and entitled "CARTRIDGE SAFETY INJECTION SYSTEM AND METHODS"; (7) Ser. No. 16/011,453, filed Jun. 18, 2018, and entitled "SYSTEM AND METHOD FOR SAFETY SYRINGE"; (8) Ser. No. 15/801,304, filed Nov. 1, 2017, and entitled "SYSTEM AND METHOD FOR SAFETY SYRINGE"; (9) Ser. No. 15/985,354, filed May 21, 2018, and entitled "SYSTEM AND METHOD FOR COLLECTING INJECTION INFORMATION"; and "(10) Ser. No. 16/683,157, filed Nov. 13, 2019, and entitled "SYSTEM AND METHOD FOR MULTIPLE SITE INJECTION". The contents of the above-mentioned applications are fully incorporated herein by reference as though set forth in full.

FIELD OF THE DISCLOSURE

The present disclosure relates generally to dispensing and/or injection systems, devices, and processes for facilitating various levels of control over fluid delivery, and more particularly to systems and methods related to dispensing and/or injection systems for serial delivery of multiple doses of dispensable or injectable substances.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a proximal/retracted position relative to the syringe body (4). The tubular needle shield (22) is "locked" in the distal/extended configuration, such that the needle shield (22) can no longer be returned to the proximal/retracted position, to prevent accidental needle sticks after injection.

Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possibly malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus, certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

As used in this application, the term fluid includes gels, jelly, creams, oils, ointments, emulsions, suspensions, dispersions, serums, semi-solids, semi-liquids, and/or liquids. These fluids may be of low or high viscosity. Some medications are serially delivered to multiple sites in or on a patient during a single treatment. In addition to systems for injecting medications, other systems (i.e., dispensing systems) serially dispense medications to multiple sites on a patient during a treatment course. The treatment course may be a single dose, or multiple doses spaced over time. There is a need for dispensing and/or injection systems which address shortcomings of currently-available configurations. In particular, there is a need for dispensing and/or injection systems that serially dispense and/or inject fluids at multiple sites on one patient. It is also desirable that such syringe assemblies may utilize the existing and relatively well-controlled supply chain of conventionally delivered pre-filled cartridges and other off-the-shelf components, and the corresponding assembly machinery and personnel.

SUMMARY

Embodiments are directed to dispensing and/or injection systems. In particular, the embodiments are directed to dispensing and/or injection systems for serial delivery of multiple doses of dispensable or injectable substances.

In one embodiment, a system for fluid delivery includes a syringe body having proximal and distal ends, a syringe interior, and a syringe flange at the proximal end thereof. The system also includes a fluid disposed in the syringe interior. The system further includes a finger flange coupled to the syringe flange. Moreover, the system includes a stopper member disposed in the syringe interior. In addition, the system includes a plunger member coupled to the stopper member and having a ratchet portion. The system also includes a push member disposed coaxially around at least a portion of the plunger member and operatively coupled thereto, the push member having an outer telescoping member disposed at a proximal end thereof. The system further includes an inner telescoping member disposed slidably and at least partially in the outer telescoping member and operatively couple thereto. Moreover, the system includes a thumbpad disposed coupled to a proximal end of the inner telescoping member.

In one or more embodiments, the finger flange includes a proximally projecting tubular member, and a distal end of the push member is disposed in the proximally projecting tubular member. The proximally projecting tubular member of the finger flange may define a proximally facing surface. The outer telescoping member of the push member may define a distally facing surface configured to interfere with the proximally facing surface of the proximally projecting tubular member of the finger flange to limit distal movements of the push member relative to the finger flange. The outer telescoping member of the push member may define a side opening having a proximally facing wall. The inner telescoping member may define a distally tapering member configured to interfere with the proximally facing wall of the side opening of the outer telescoping member of the push member to limit distal movement of the inner telescoping member relative to the outer telescoping member of the push member.

In one or more embodiments, the system also includes a distal spring disposed in the proximally projecting tubular member of the finger flange and between and in contact with the finger flange and the push member. The system of claim 5 may include a proximal spring disposed in the outer telescoping member of the push member between and in contact with the push member and the inner telescoping member. The distal spring may be weaker than the proximal spring, with less pre-load in a resting state, such that applying a distally directed force to the inner telescoping member through the thumbpad initially compresses the distal spring until the distally facing surface of the push member abuts the proximally facing surface of the proximally projecting tubular member of the finger flange before compressing the proximal spring to allow the inner telescoping member to move distally relative to the outer telescoping member. The distal spring may be stronger than the proximal spring, with more pre-load in a resting state, such that applying a distally directed force to the inner telescoping member through the thumbpad initially compresses the proximal spring until the distally tapering member of the inner telescoping member abuts the proximally facing wall of the outer telescoping member of the push member before compressing the distal spring to allow the push member to move distally relative to the finger flange. The distal spring and proximal spring may have equal strength, such that the push member and the inner telescoping member move simultaneously. The distal and proximal springs having the same strength allow for a smooth ejection force profile, with no perceptible difference between the motion of the push member and the inner telescoping member and thumbpad.

In one or more embodiments, the push member includes a distally extending pawl in contact with and operatively coupled to the ratchet portion of the plunger member. The ratchet portion of the plunger member may include a plurality of teeth. A full depression of the thumbpad relative to the finger flange may advance the plunger member distally relative to the syringe body by a distance of one tooth of the plurality of teeth.

The aforementioned and other embodiments of the invention are described in the Detailed Description which follows.

Figure 1A:
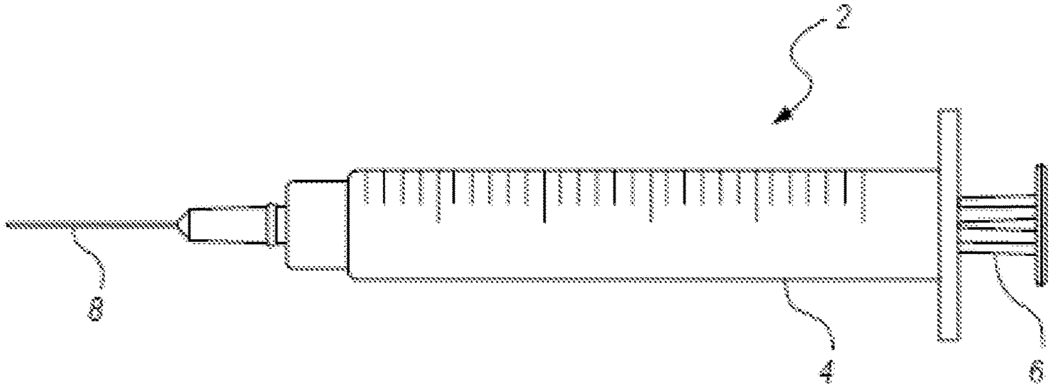
FIGS. 1A to 5C illustrate various aspects of conventional injection syringe configurations.
Figure 1B:
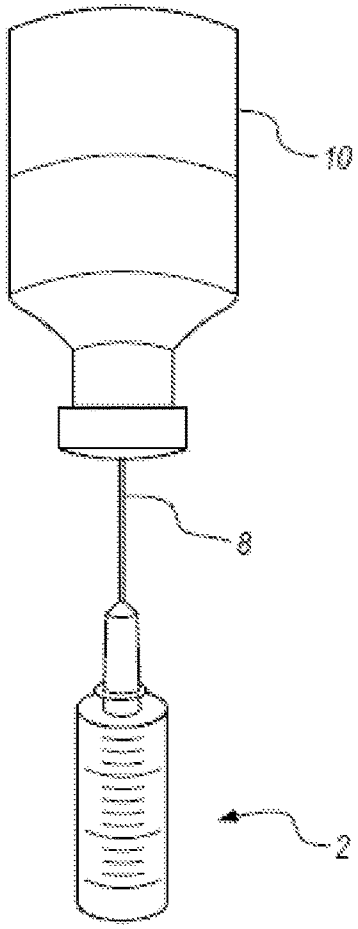
Figure 2A:
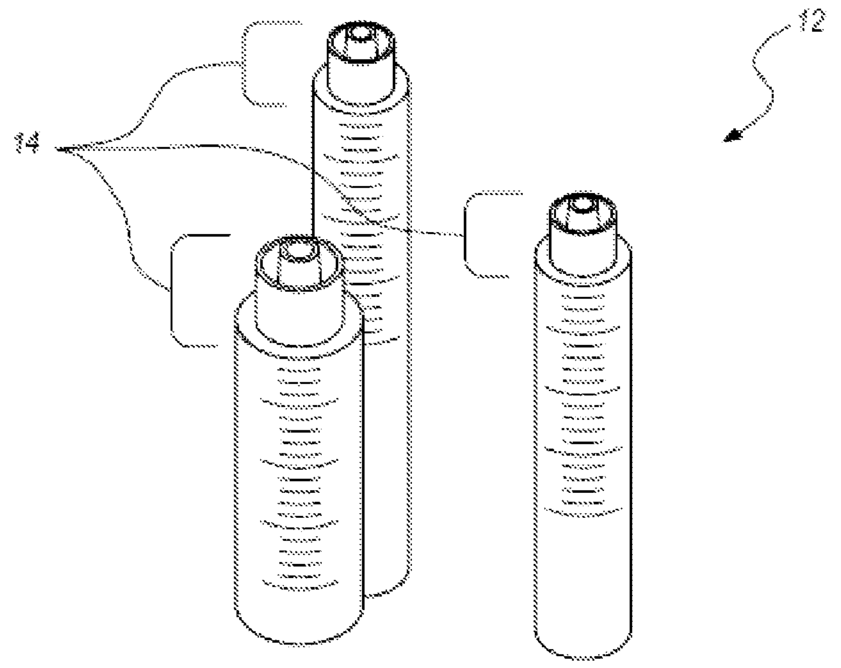
Figure 2B:
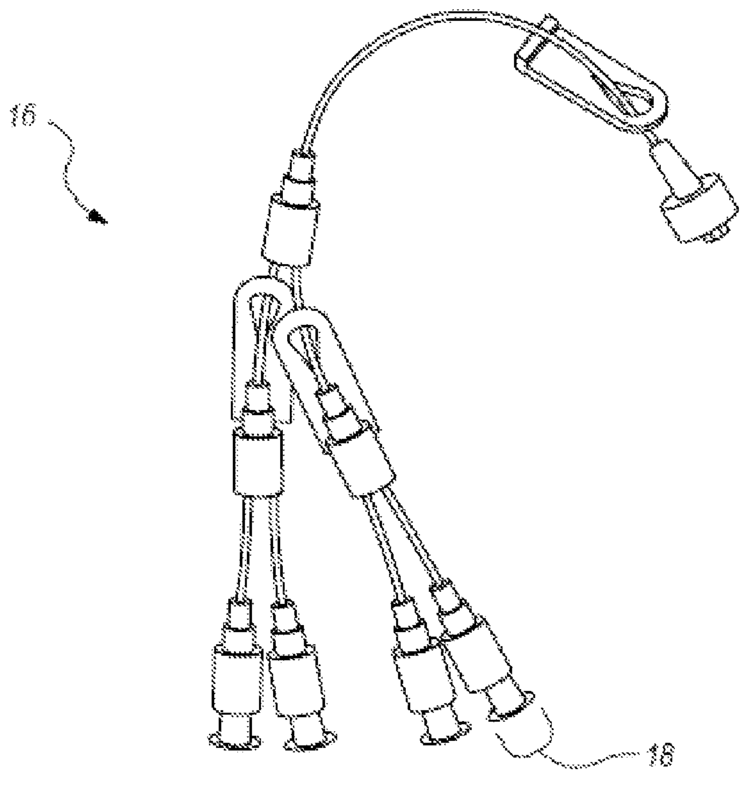
Figure 3:
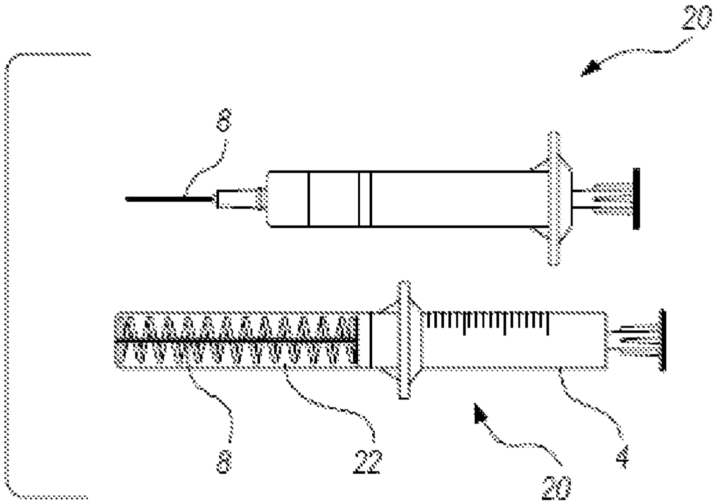
Figure 4A:
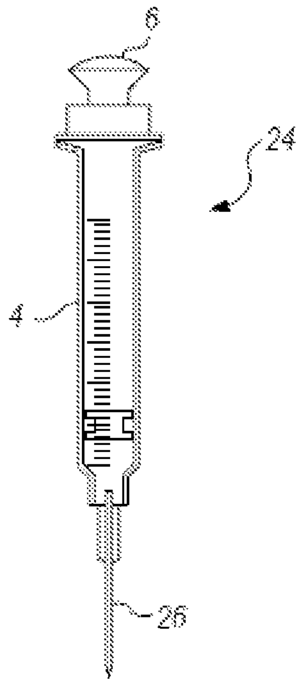
Figure 4B:
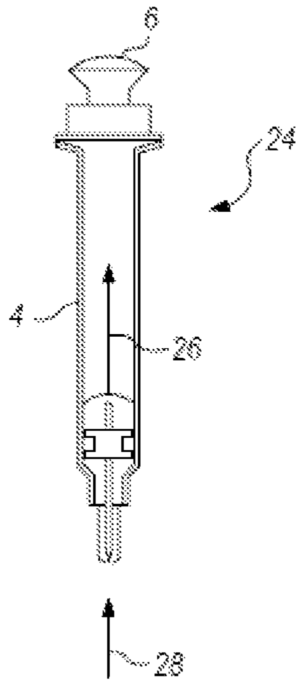
Figure 5A:
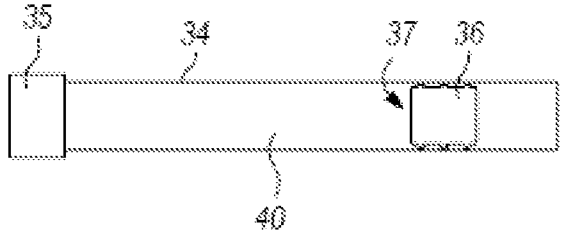
Figure 5B:
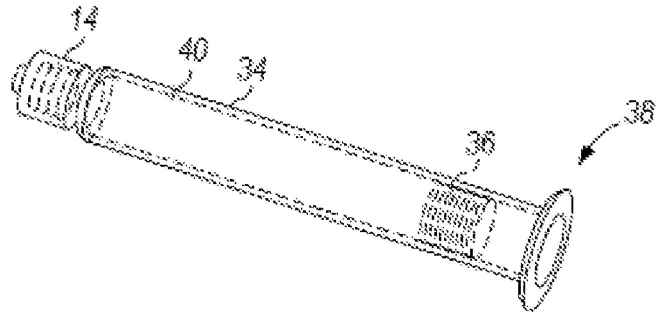
Figure 5C:
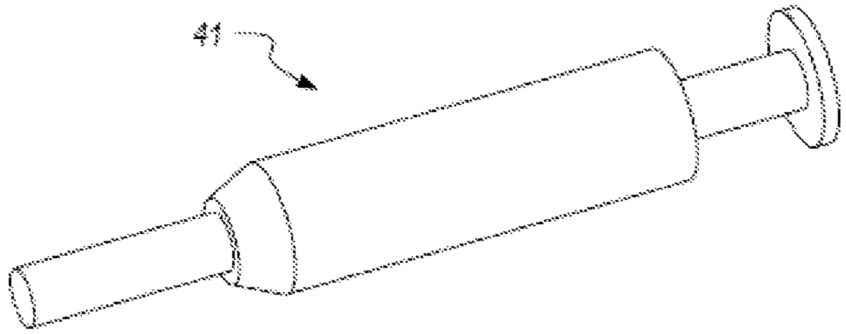

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Multiple Site Dispensing and/or Injection systems

Many dispensable or injectable medications can be administered to multiple dispensing, application, and/or injection sites on the same patient. Some medical procedures involve serial dispensing, application, and/or injection of fixed volumes (e.g., 0.1 ml and/or microliter range volumes) of medications (e.g., botulinum toxin or "Botox") at multiple dispensing, application, and/or injection sites on a patient. Currently, many medicines are drawn into an dispensing and/or injection system from a vial, which increases procedure time and exposure of a needle for unintended punctures. Further, some medications are delivered in a viscous solution, and therefore require a larger diameter (e.g., lower gauge: 25*g*) needle to be used to draw the viscous medication into the dispensing and/or injection system and a smaller diameter (e.g., higher gauge: 30*g*, 32*g*, 34*g*, sub-34*g*) needle to be use for an injection. This exchange of needles results in increased procedure time and risk of unintended punctures. The multiple site dispensing and/or injection system described herein addresses these issues of current systems.

Figure 6:
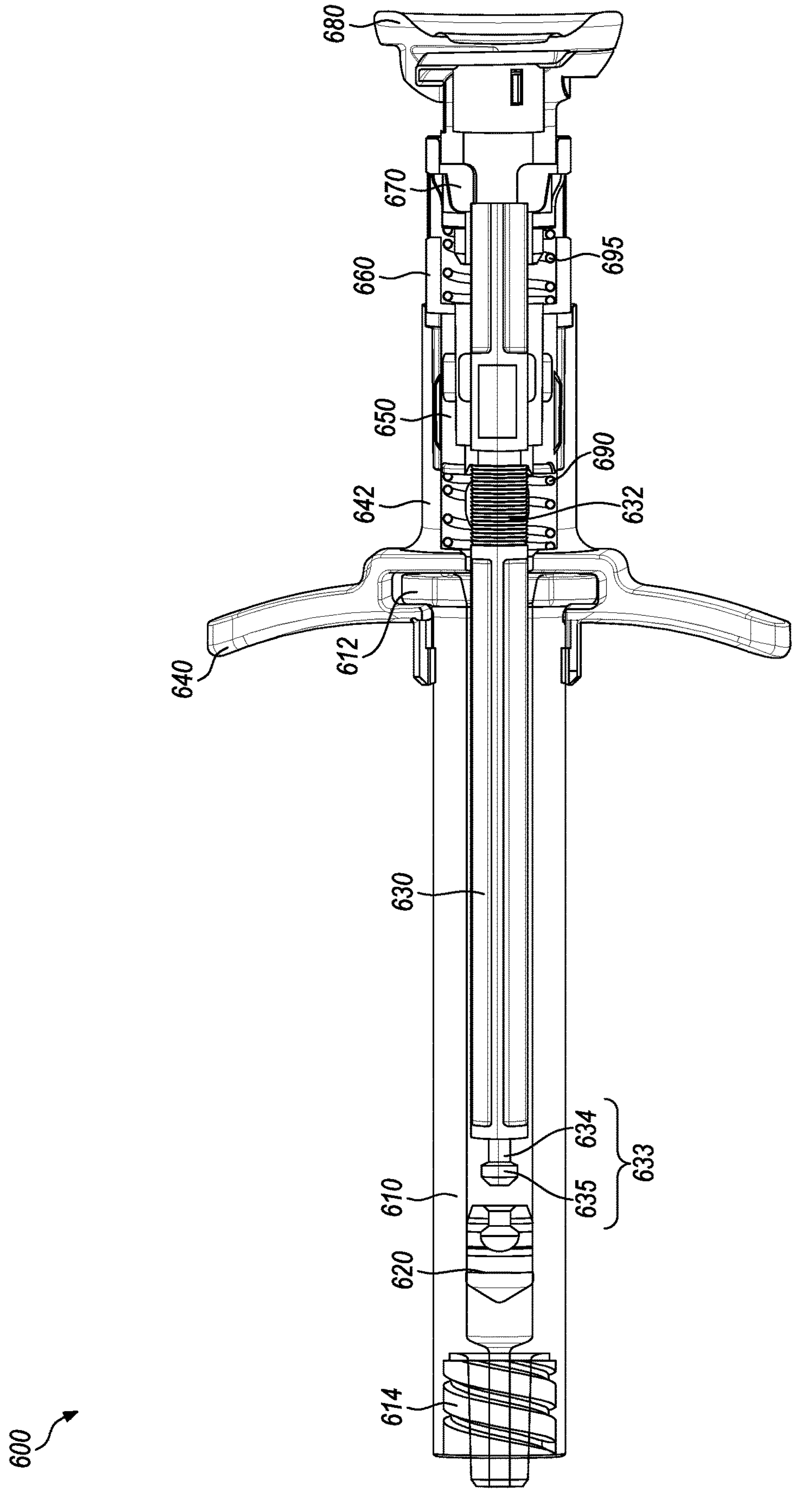
FIG. 6 is a longitudinal cross-sectional view of the multiple site dispensing and/or injection system according to some embodiments.

FIGS. 6-15 depict a multiple site dispensing and/or injection system 600 according to some embodiments. As shown in FIG. 6, the system 600 can be prefilled with an dispensable or injectable medication. The system 600 includes a syringe body 610, a stopper member 620, a plunger member 630, and a finger flange 640. The syringe body 610 includes a syringe flange 612 at a proximal end thereof on which the finger flange 640 is coupled. The syringe body 610 also includes a needle hub coupling member 614 (e.g., a female Luer connector) configured to removably couple a needle hub (not shown) including a needle (not shown), other dispensing mechanism (not shown), or applicator tip (see FIGS. 16 to 20) thereto.

Many of these system components (e.g., the syringe body 610 and the stopper member 620, and needle hub (not shown)) may be off-the-shelf components to utilize the existing and relatively well-controlled supply chain, and the corresponding assembly machinery and personnel. The syringe body 610 may be glass, metal, or polymeric materials such as COC, COP, polypropylene, polyethylene, or other syringe material. The stopper member 620 may be rubber such as butyl, chlorobutyl, bromobutyl, or a polymeric material such as a thermoplastic elastomer. The stopper member 620 may be covered in a protective and/or lubricious coating such as PTFE or other polymer. The stopper member 620 being off-the-shelf refers to a commercially available stopper member, which has a generally smooth distally facing surface which contains no projections or recesses for coupling to a needle.

The system 600 also includes a push member 650 configured to apply distally directed force to the plunger member 630 and the stopper member 620 coupled thereto. The stopper member 620 and plunger member 630 are shown separated for clarity in FIG. 6. The distal end of the plunger member 630 comprises a distal spike 633 which is configured to engage into the stopper member 620. The distal spike 633 of the plunger member 630 comprises a shaft 634 and a head 635 configured to resist pullout of the plunger member 630 from the stopper member 620. In an alternative embodiment, the distal end of the plunger member 630 may comprise a threaded connection (not shown) with the stopper member 620 or may be flat (not shown) and rest on the stopper member 620. The push member 650 includes an outer telescoping member 660 at a proximal end thereof. The system 600 further includes an inner telescoping member 670 disposed slidably and at least partially within the outer telescoping member 660. Moreover, the system 600 includes a thumbpad 680 coupled to a proximal end of the inner telescoping member 670.

The finger flange 640 includes a proximally projecting tubular member 642. A distal end of the push member 650 is disposed slidably in the proximally projecting tubular member 642. Similarly, a distal end of the inner telescoping member 670 is disposed slidably within the outer telescoping member 660 defined by the push member 650.

Figure 7:
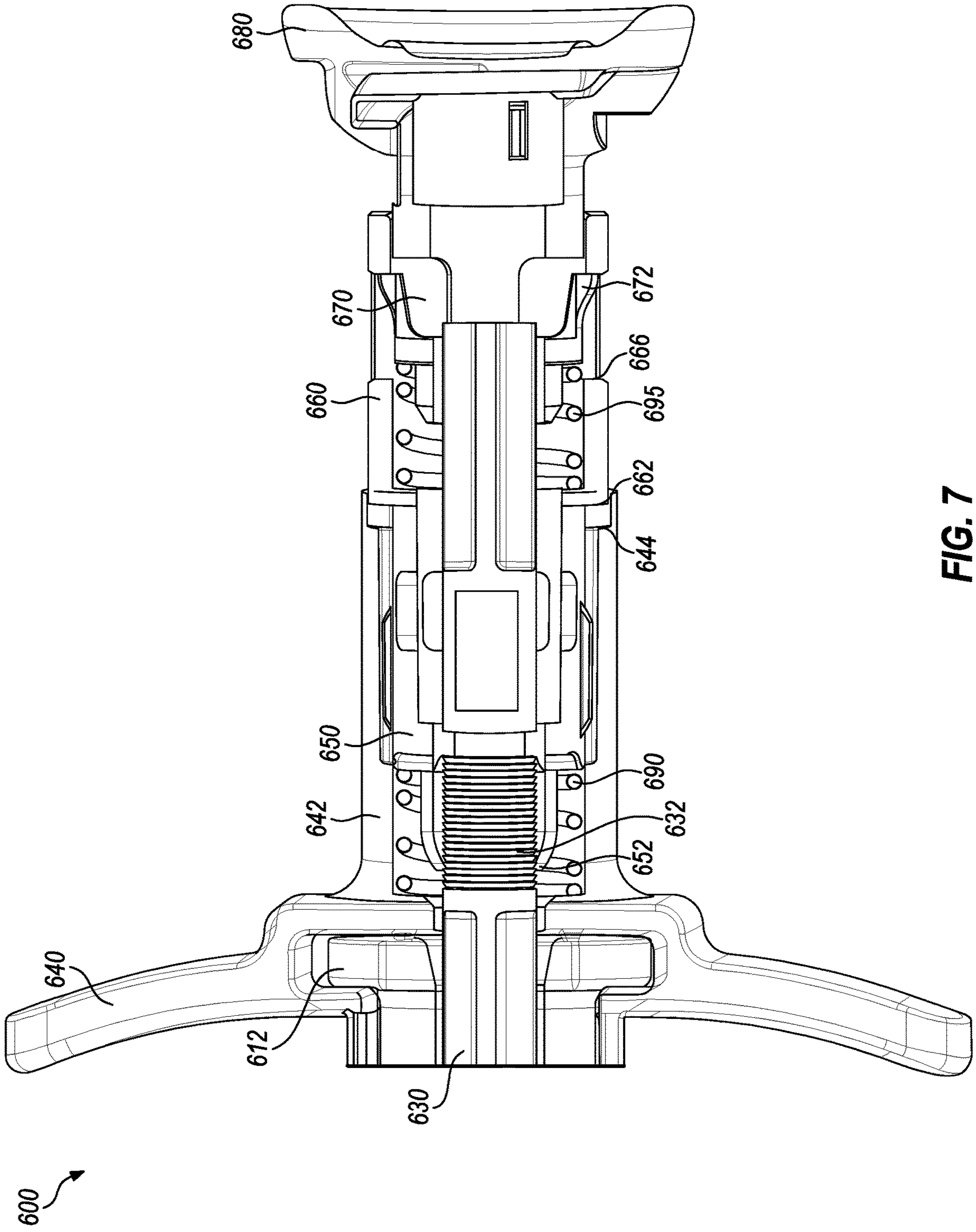
FIG. 7 is a detailed longitudinal cross-sectional view of the multiple site dispensing and/or injection system depicted in FIG. 6.

FIG. 7 is a detailed longitudinal cross-sectional view of the multiple site dispensing and/or injection system 600 depicted in FIG. 6. As shown in FIG. 7, the proximally projecting tubular member 642 of the finger flange 640 defines a proximally facing surface 644. The outer telescoping member 660 of the push member 650 defines a distally facing surface 662 configured to interfere with the proximally facing surface 644 of the proximally projecting tubular member 642 of the finger flange 640 to limit distal movement of the push member 650 relative to the finger flange 640. Accordingly, the push member 650 can only move distally relative to the finger flange 640 a distance defined by the distance between the proximally facing surface 644 of the proximally projecting tubular member 642 of the finger flange 640 and the distally facing surface 662 of the outer telescoping member 660 of the push member 650.

As also shown in FIG. 7, the outer telescoping member 660 of the push member 650 defines a side opening 664 having a proximally facing wall 666. The inner telescoping member 670 defines a distally tapering member 672 configured to interfere with the proximally facing wall 666 of the side opening 664 of the outer telescoping member 660 of the push member 650 to limit distal movement of the inner telescoping member 670 relative to the outer telescoping member 660 of the push member 650. Accordingly, the inner telescoping member 670 can only telescope distally into the outer telescoping member 660 a distance defined by the distance between the proximally facing wall 666 of the side opening 664 of the outer telescoping member 660 of the push member 650 and the distally tapering member 670 of the inner telescoping member 670.

The system 600 also includes a distal spring 690 disposed in the proximally projecting tubular member 642 of the finger flange 640 between and in contact with the finger flange 640 and the push member 650. The distal spring 690 biases the push member 650 proximally away from the finger flange 640. The system 600 also includes a proximal spring 695 disposed in the outer telescoping member 660 defined by the push member 650 between and in contact with the push member 650 and the inner telescoping member 670. The proximal spring 695 biases the inner telescoping member 670 proximally away from the outer telescoping member 660 and the push member 650. In embodiments where the distal spring 690 is weaker than the proximal spring 695, applying a distally directed force to the inner telescoping member 670 through the thumbpad 690 transfers the force through the proximal spring 695 to the push member 650. This transferred force moves the push member 650 distally relative to the finger flange 640 and compresses the distal spring 690 until the distally facing surface 662 of the outer telescoping member 660 of the push member 650 abuts the proximally facing surface 644 of the proximally projecting tubular member 642 of the finger flange 640, preventing further distal movement of the push member 650 relative to the finger flange 640. Continued application of distally directed force compresses the proximal spring 695 to allow the inner telescoping member 670 to telescope distally into the outer telescoping member 660.

Figure 8:
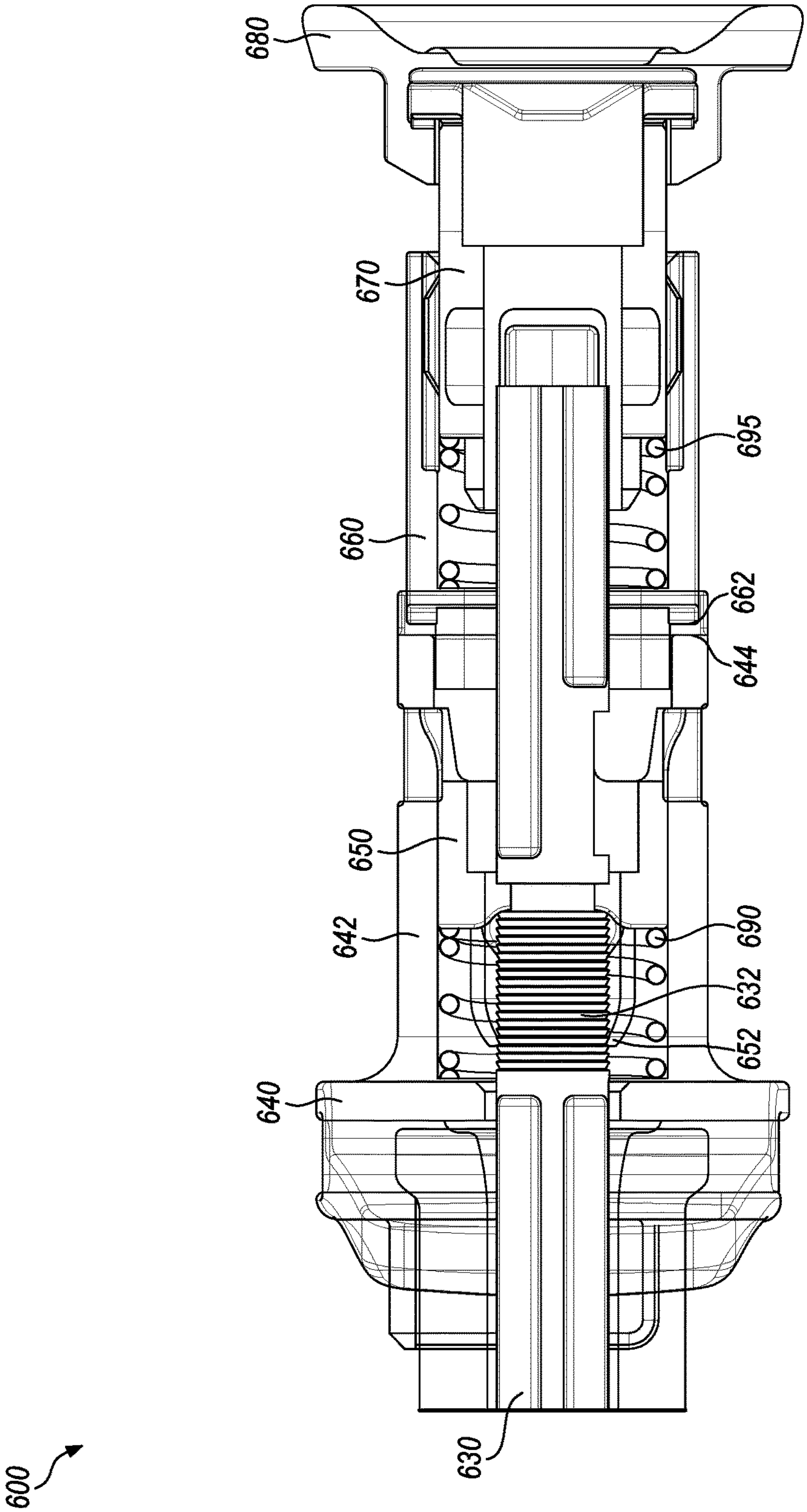
FIG. 8 is a detailed longitudinal cross-sectional view, taken along a plane orthogonal to the cross-section plane in FIG. 7, of the multiple site dispensing and/or injection system depicted in FIGS. 6 and 7.

FIG. 8 is a detailed longitudinal cross-sectional view, taken along a plane orthogonal to the cross-section plane in FIG. 7, of the multiple site dispensing and/or injection system 600 depicted in FIGS. 6 and 7. As shown in FIG. 8, the proximal end of the push member 650 defines a pair of distally extending pawls 652 in contact with an operatively coupled to the ratchet portion 632 of the plunger member 630. The pawls 652 may be made of metal or polymer. The ratchet portion 632 of the plunger member 630 includes a plurality of teeth 634 that taper in a distal direction. As such, when the push member 650 moves distally, the pair of distally extending pawls 652 push the respective teeth 634 and the plunger member 630 attached thereto in a distal direction. When the push member 650 is returned proximally by the distal spring 690, the pair of distally extending pawls 652 can ride over the respective teeth 634 and move one set of teeth 634 in a proximal direction. Advancing the plunger member 630 ejects a predetermined dose of dispensable and/or injectable fluid from the syringe body 610. Returning the pair of distally extending pawls 652 to a proximal position adjacent the next pair of teeth 634 in a proximal direction and prepares the system 600 to eject the next dose of dispensable and/or injectable fluid in a serial manner.

FIGS. 9 to 15 depict an exemplary method of operating a multiple site dispensing and/or injection system 600 to advance a plunger member 630 to eject a predetermined dose of dispensable and/or injectable fluid from a syringe body 610 while preparing the system 600 to eject the next dose of dispensable and/or injectable fluid in a serial manner. In the dispensing and/or injection system 600 depicted in FIGS. 9 to 15, the distal spring 690 is weaker than the proximal spring 695. In other embodiments, the springs 690, 695 may have equal strength, or the distal spring 690 may be stronger than the proximal spring 695. In such cases, the sequence of motions would be different, but the overall operation and function of the device would remain the same. The springs 690, 695 can be tuned to achieve a variety of force profiles.

Figure 9:
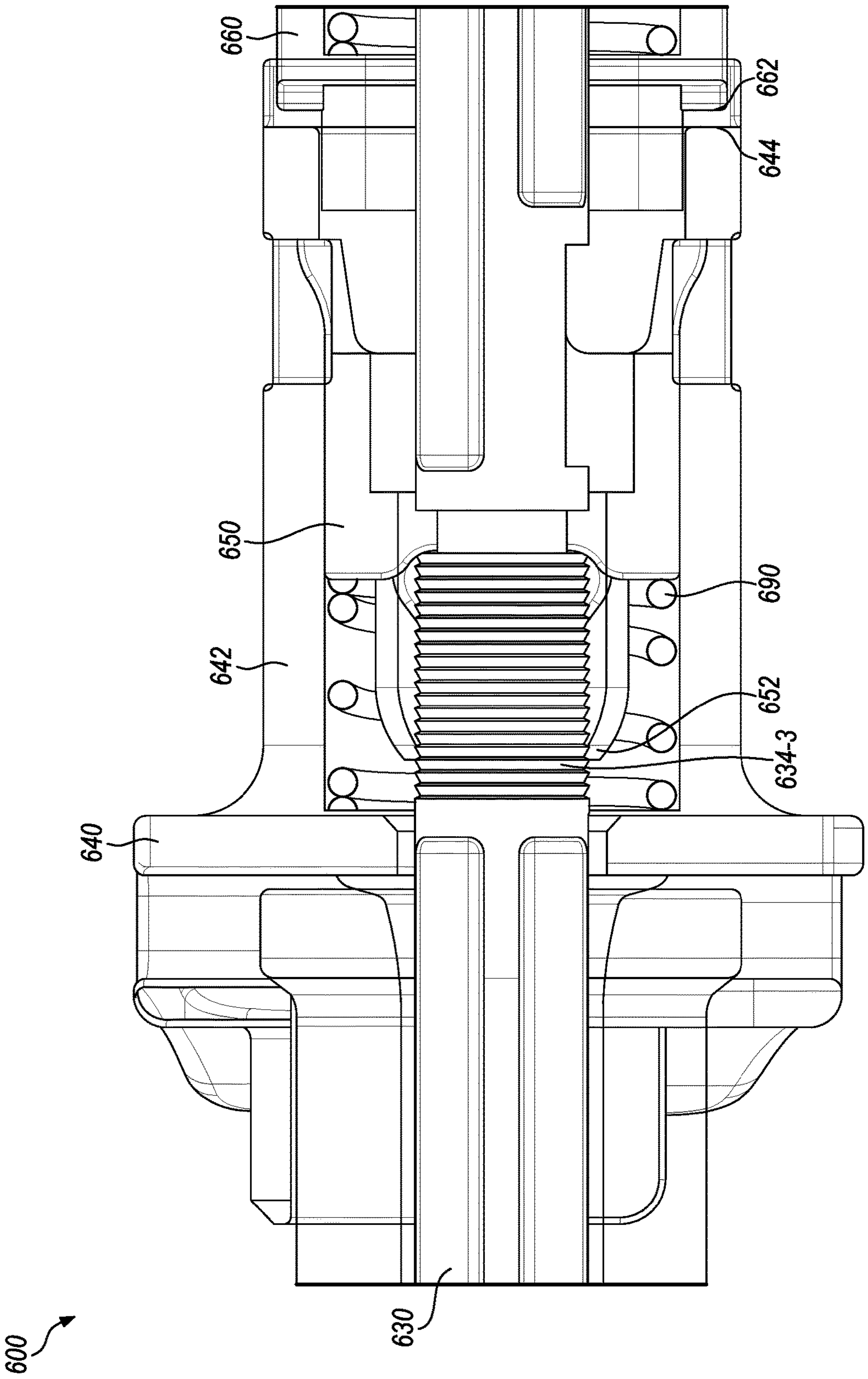
FIGS. 9 and 14 are detailed and even more detailed longitudinal cross-sectional views, taken along the same cross-section plane as FIG. 8, of a multiple site dispensing and/or injection system ready to deliver a fourth dose of dispensable or dispensable or injectable fluid.
Figure 14:
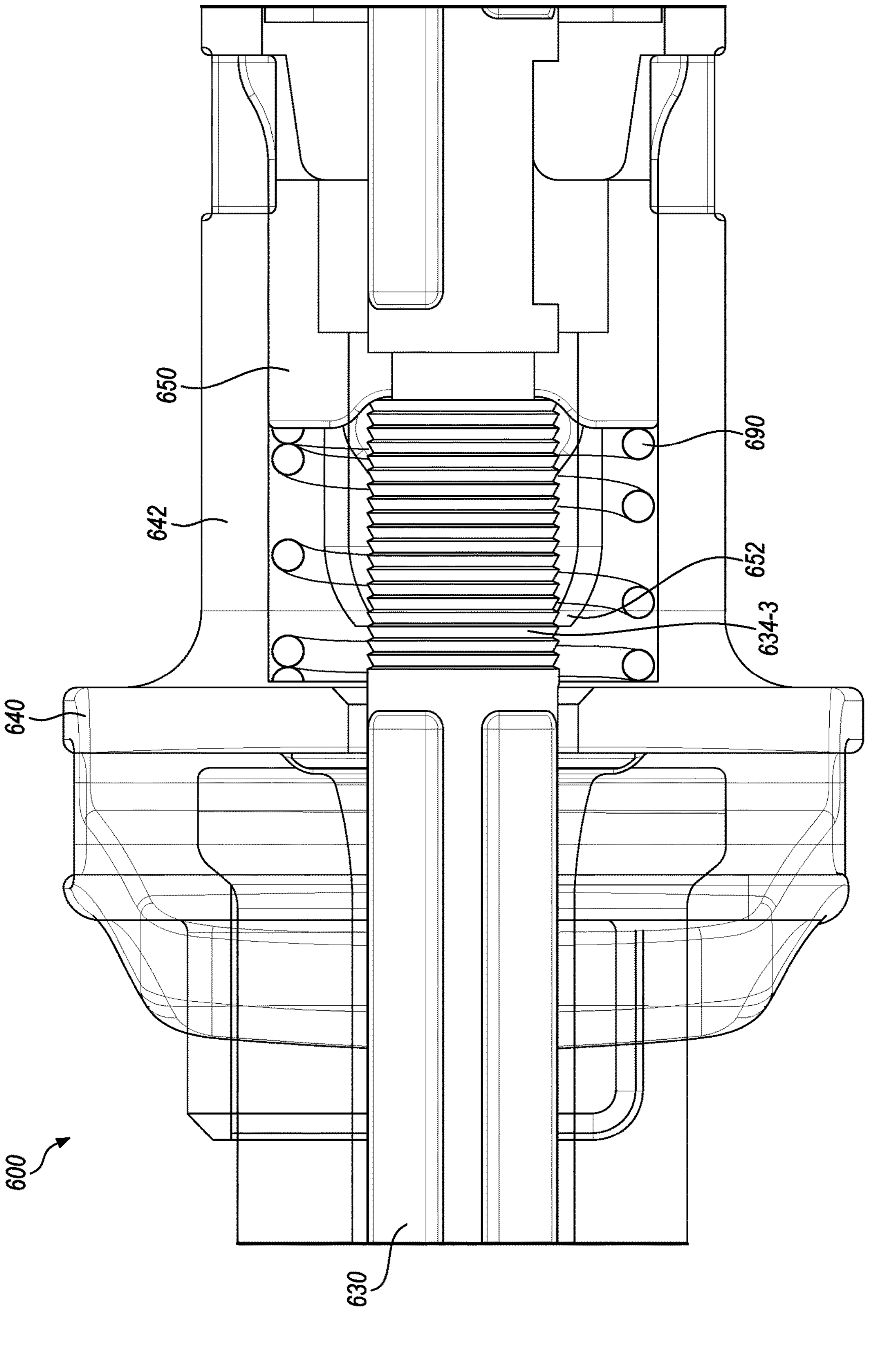

FIG. 9 is a detailed longitudinal cross-sectional view, taken along the same cross-section plane as FIG. 8, of the multiple site dispensing and/or injection system 600 depicted in FIGS. 6 to 8 after the system 600 has delivered three predetermined doses of dispensable and/or injectable fluid from the syringe body 610 and the system 600 is ready to deliver a fourth dose of dispensable and/or injectable fluid. As such, the pair of distally directed pawls 652 are disposed just proximal of the third pair of teeth 634-3. FIG. 14 is an even more longitudinal cross-sectional view system 600 showing the relative positions of the pair of distally directed pawls 652 and the third pair of teeth 634-3. Further, the gap between the proximally facing surface 644 of the proximally projecting tubular member 642 of the finger flange 640 and the distally facing surface 662 of the outer telescoping member 660 of the push member 650 is expanded because the push member 650 has been moved distally by the distal spring 690 to prepare system 600 to deliver the next dose.

Figure 10:
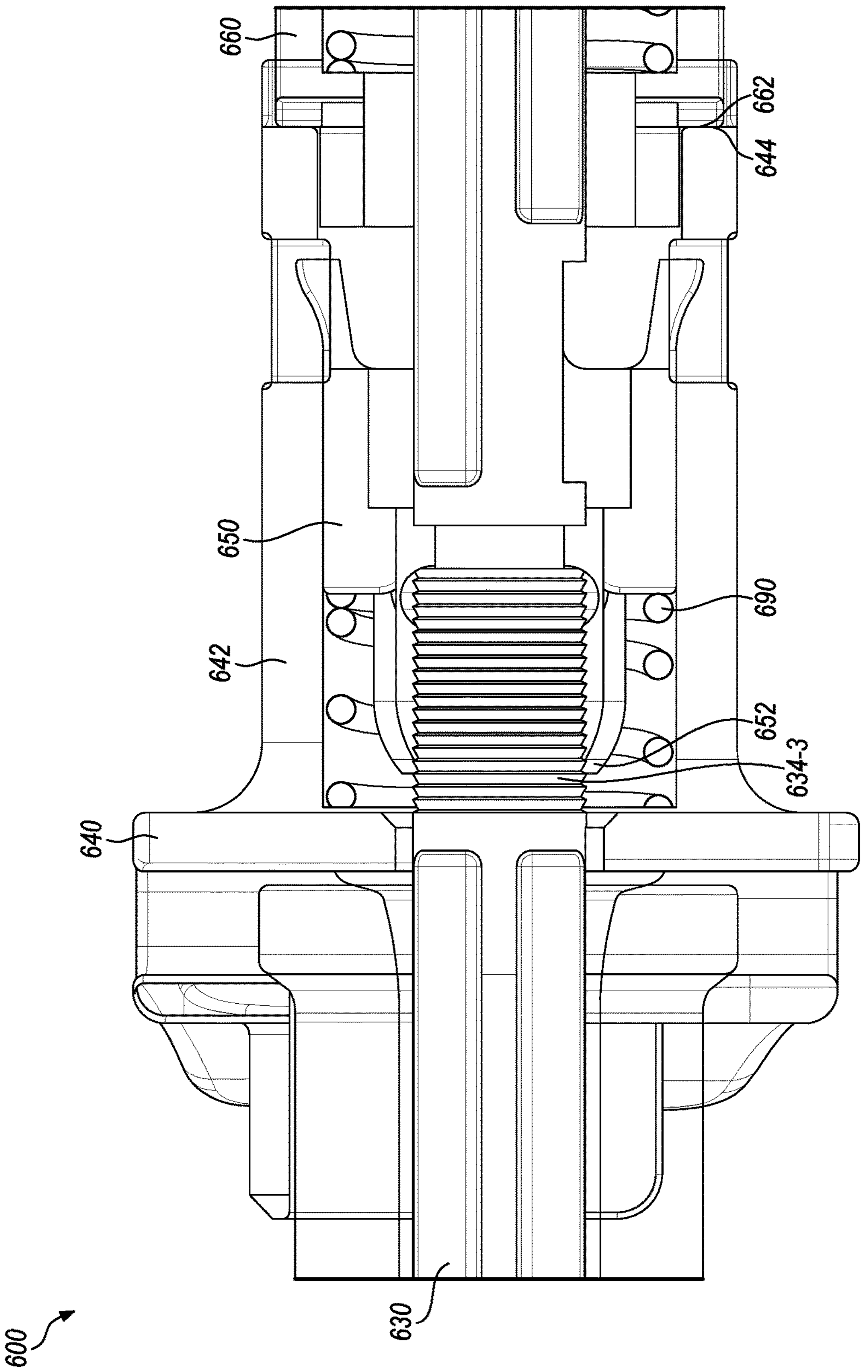
FIG. 10 is a detailed longitudinal cross-sectional view, taken along the same cross-section plane as FIG. 8, of the multiple site dispensing and/or injection system depicted in FIG. 9 after the fourth dose of dispensable or injectable fluid has been delivered.

FIG. 10 is a detailed longitudinal cross-sectional view, taken along the same cross-section plane as FIG. 8, of the multiple site dispensing and/or injection system 600 depicted in FIGS. 6 to 9 after a distally directed force has been applied (through the thumb 680, the inner telescoping member 670, and the proximal spring 695-see FIG. 7) to the push member 650. The distally directed force moves the push member 650 and the outer telescoping member 660 forming a part thereof distally. This eliminates the gap between the proximally facing surface 644 of the proximally projecting tubular member 642 of the finger flange 640 and the distally facing surface 662 of the outer telescoping member 660 of the push member 650. This also causes the pair of distally directed pawls 652 to push the third pair of teeth 634-3 and the plunger member 630 attached thereto distally a distance equal to the gap between the proximally facing surface 644 of the proximally projecting tubular member 642 of the finger flange 640 and the distally facing surface 662 of the outer telescoping member 660 of the push member 650. This gap is slightly larger than the distance between two teeth 634 on the ratchet portion 632 of the plunger member 630 to provide tolerance for the machining of these small parts.

Figure 11:
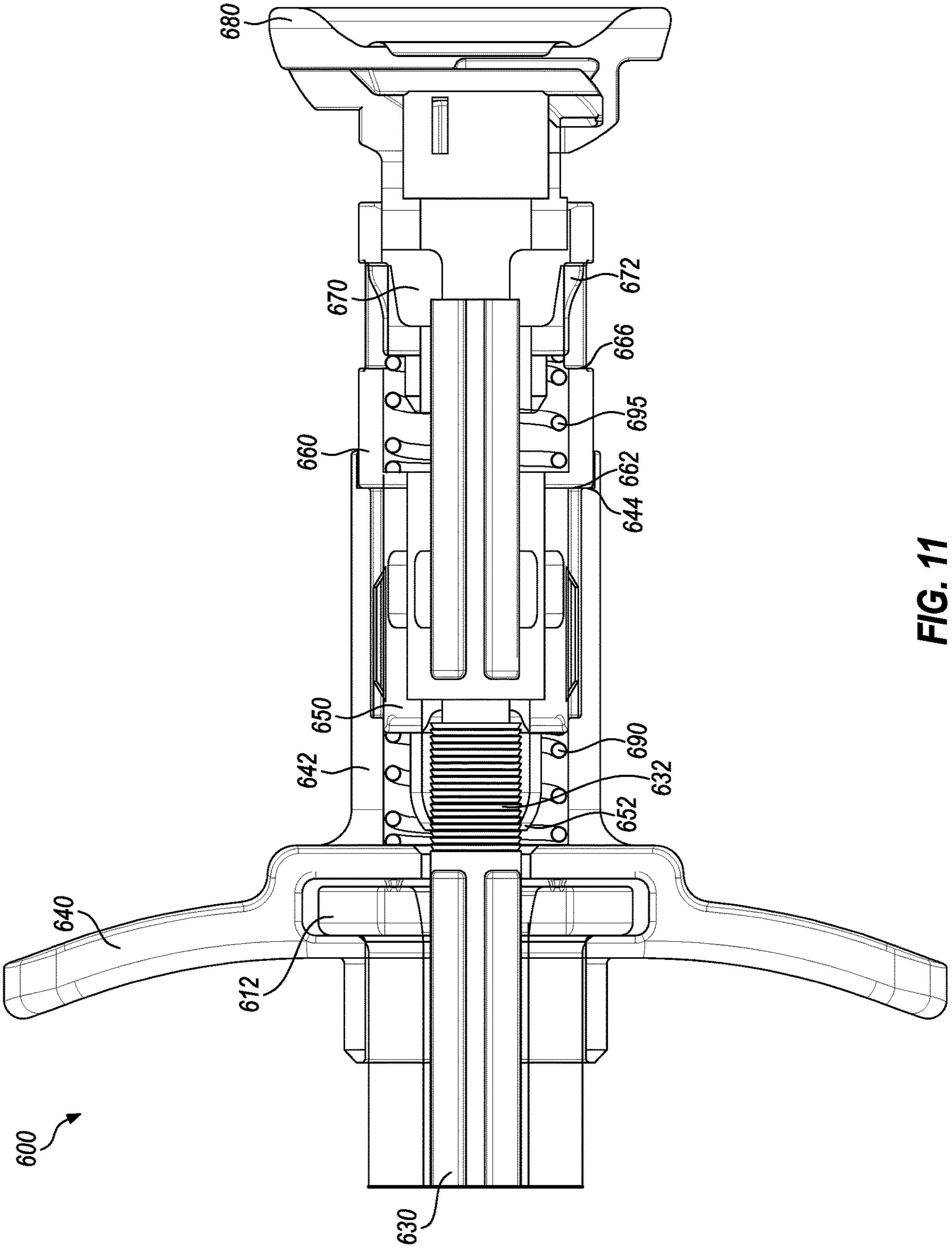
FIG. 11 is a detailed longitudinal cross-sectional view, taken along the same cross-section plane as FIG. 7 (which is orthogonal to the cross-section plane in FIG. 8), of the multiple site dispensing and/or injection system depicted in FIG. 9 in the same configuration as that depicted in FIG. 10.

FIG. 11 is a detailed longitudinal cross-sectional view, taken along the same cross-section plane as FIGS. 6 and 7 (which is orthogonal to the cross-section plane in FIGS. 8 to 10), of the multiple site dispensing and/or injection system 600 depicted in FIGS. 6 to 10 in the same configuration as that depicted in FIG. 10. The gap between the proximally facing surface 644 of the proximally projecting tubular member 642 of the finger flange 640 and the distally facing surface 662 of the outer telescoping member 660 of the push member 650 is eliminated, preventing further distal movement of the push member 650 relative to the finger flange 640. However, a second gap still exists between the distally tapering member 672 of the inner telescoping member 670 and the proximally facing wall 666 of the side opening 664 of the outer telescoping member 660 of the push member 650. The second gap allows the telescope distally inside of the outer telescoping member 660 of the push member 650, thereby compressing the proximal spring 695. The relative spring forces of the distal and proximal springs 690, 695 are tuned such that a typical user could not distinguish between compressing the distal spring 690 (and delivering a dose of dispensable and/or injectable fluid) and compressing the proximal spring 695 (and telescoping the inner and outer telescoping members 670, 660 together).

Figure 12:
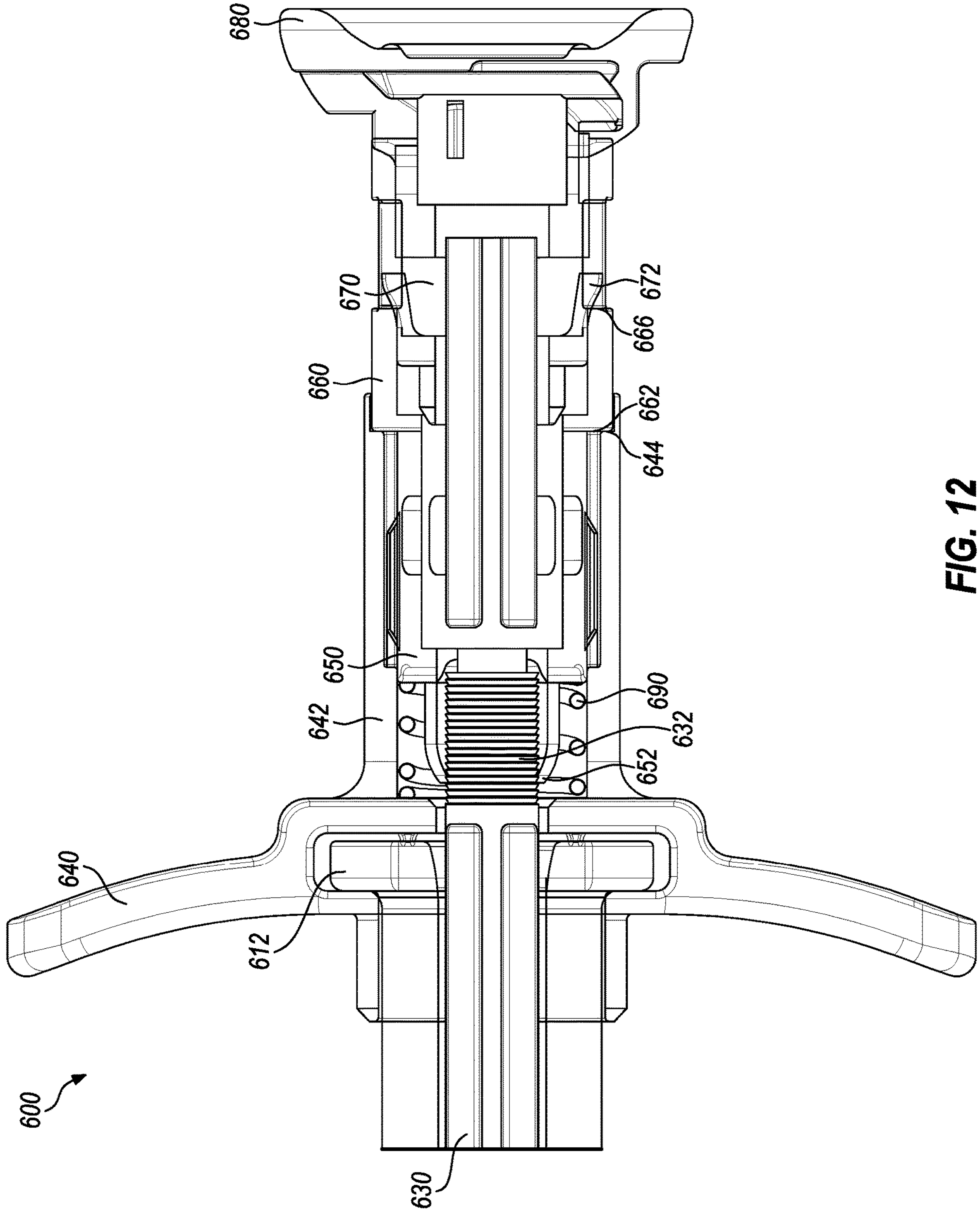
FIG. 12 is a detailed longitudinal cross-sectional view, taken along the same cross-section plane as FIG. 7 (which is orthogonal to the cross-section plane in FIG. 8), of the multiple site dispensing and/or injection system depicted in FIG. 9 in the after a complete stroke including the portion of the stroke telescoping the inner and outer telescoping members together.

FIG. 12 is a detailed longitudinal cross-sectional view, taken along the same cross-section plane as FIG. 11, of the multiple site dispensing and/or injection system 600 depicted in FIGS. 6 to 11 after further distally directed force and telescoping of the inner and outer telescoping members 670, 660 together have eliminated the second gap between the distally tapering member 672 of the inner telescoping member 670 and the proximally facing wall 666 of the side opening 664 of the outer telescoping member 660 of the push member 650. Telescoping of the inner and outer telescoping members 670, 660 together provides a longer stroke relative to the length of one tooth 634 to provide improved tactile feedback to a user.

Figure 13:
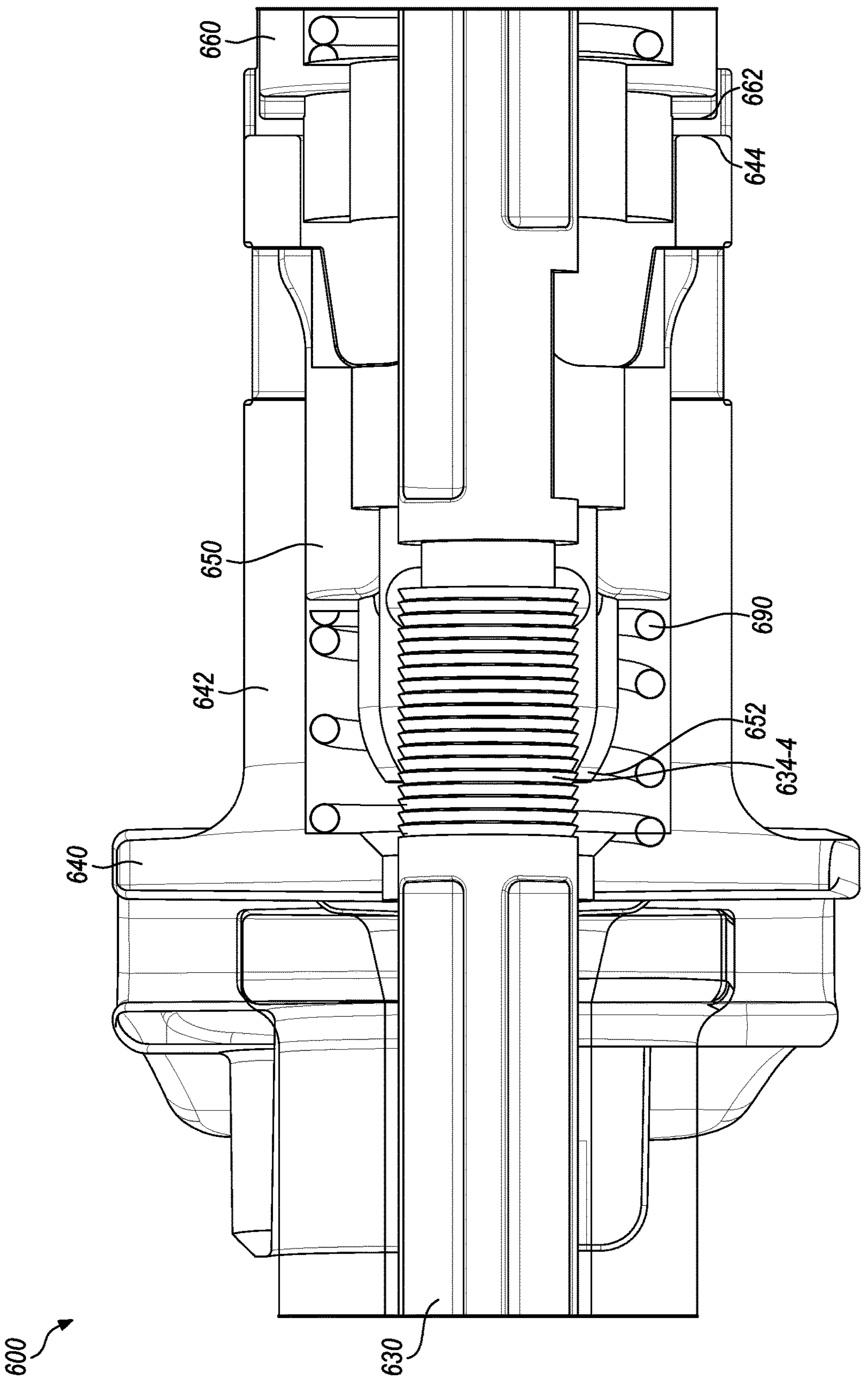
FIGS. 13 and 15 are detailed and even more detailed longitudinal cross-sectional views, taken along the same cross-section plane as FIG. 8, of a multiple site dispensing and/or injection system after springs have returned its push member and inner telescoping member to proximal positions and the system is ready to deliver a fifth dose of dispensable or injectable fluid.
Figure 15:
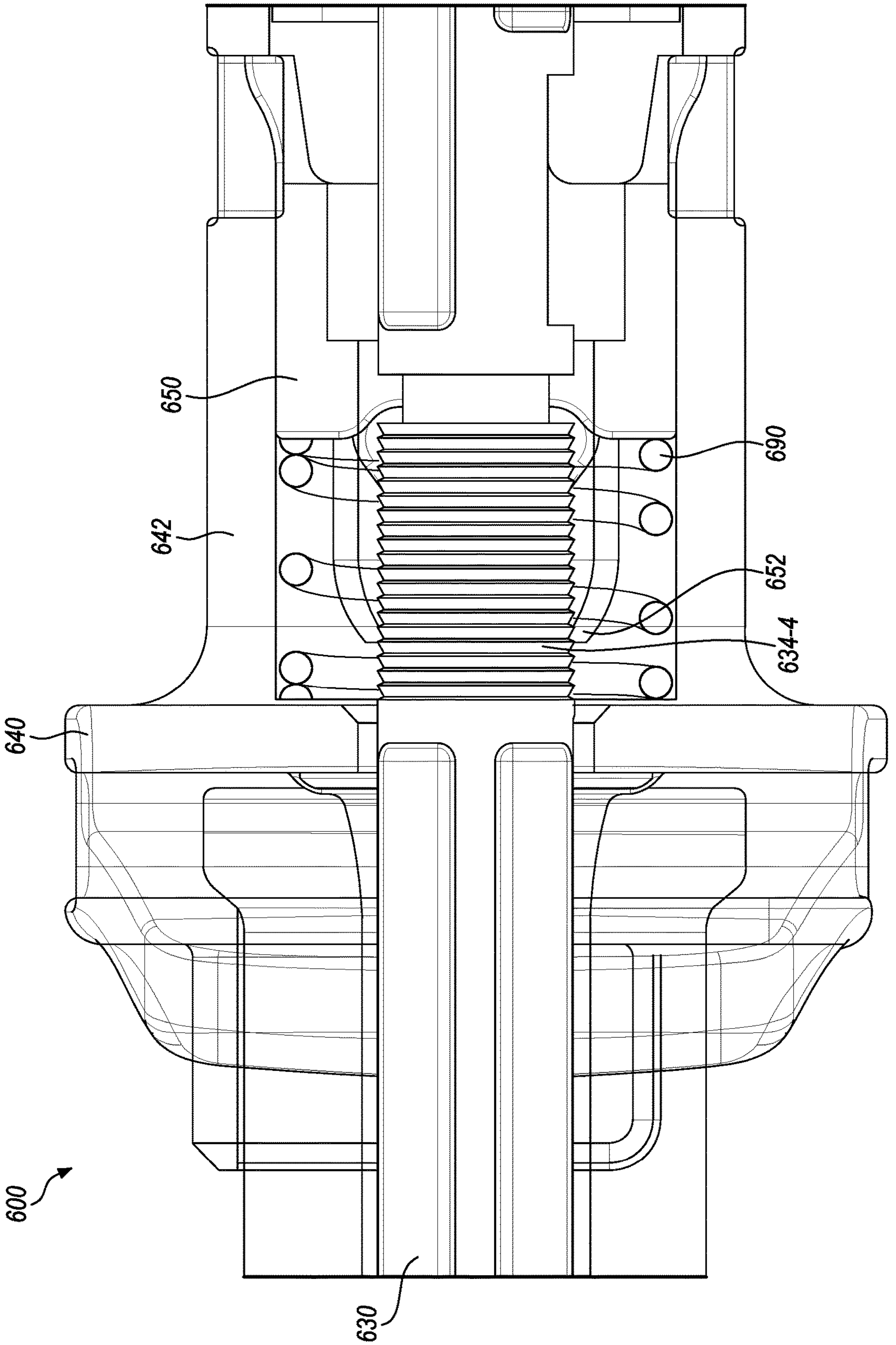

FIGS. 13 and 15 are detailed and even more detailed longitudinal cross-sectional views, taken along the same cross-section plane as FIG. 8 (which is orthogonal to the cross-section plane in FIGS. 11 and 12), of the multiple site dispensing and/or injection system 600 depicted in FIGS. 6 to 12 after the distally directed force has been removed from the system 600 and the distal and proximal springs 690, 695 have returned the push member 650 and the inner telescoping member 672 their respective proximal positions. Returning the push member 650 to its proximal position moves the pair of distally extending pawls 652 to a proximal position adjacent the next pair of teeth 634 in a proximal direction (i.e., the fourth pair of teeth 634-4). Resetting the push member 650 and the inner telescoping member 672 their respective proximal positions prepares the system 600 to eject the next dose of dispensable and/or injectable fluid in a serial manner.

While the embodiments depicted in FIGS. 9 to 15 include distal springs 690 that are weaker than proximal spring 695, in other embodiments the distal spring 690 is stronger than the proximal spring 695. In such embodiments, applying a distally directed force to the inner telescoping member 670 through the thumbpad 690 transfers first compresses the proximal spring 695, thereby telescoping the inner telescoping member 670 into the outer telescoping member 660. Only after the distally tapering member 672 of the inner telescoping member 670 abuts and interferes with the proximally facing wall 666 of the side opening 664 of the outer telescoping member 660 of the push member 650 does the distally directed force transmit through the inner telescoping member 670 to move the push member 650 distally. Continued application of distally directed force moves the push member 650 distally relative to the finger flange 640 two deliver a dose of dispensable and/or injectable fluid. This compresses the distal spring 690 until the distally facing surface 662 of the outer telescoping member 660 of the push member 650 abuts the proximally facing surface 644 of the proximally projecting tubular member 642 of the finger flange 640, preventing further distal movement of the push member 650 relative to the finger flange 640 two arrive at the end of the stroke.

In other embodiments, the distal and proximal springs 690, 695 may also have the same strength, allowing for a smooth ejection force profile, with no perceptible difference between the motion of the push member 650 and the inner telescoping member 670 and thumbpad 680. While some embodiments are described as compressing one spring (e.g., the weaker spring) before compressing the other (e.g., the stronger spring), in other embodiments, both the distal and proximal springs 690, 695 compress/collapse simultaneously. The distal and proximal springs 690, 695 may compress/collapse at different rates depending on their strength. In some embodiments, after the gap between the distally facing surface 662 of the outer telescoping member 660 of the push member 650 and the proximally facing surface 644 of the proximally projecting tubular member 642 of the finger flange 640 is closed, the inner telescoping member 670 continues to move for a relatively large travel for improved user feedback. The relative strength of each spring 690, 695 can be tuned to provide any desired force profile. While the springs 690, 695 are shown as coil springs to be loaded in compression, alternative springs such as extension springs and/or leaf springs may be used in various embodiments.

Applicator Tip and Cap

Figure 16:
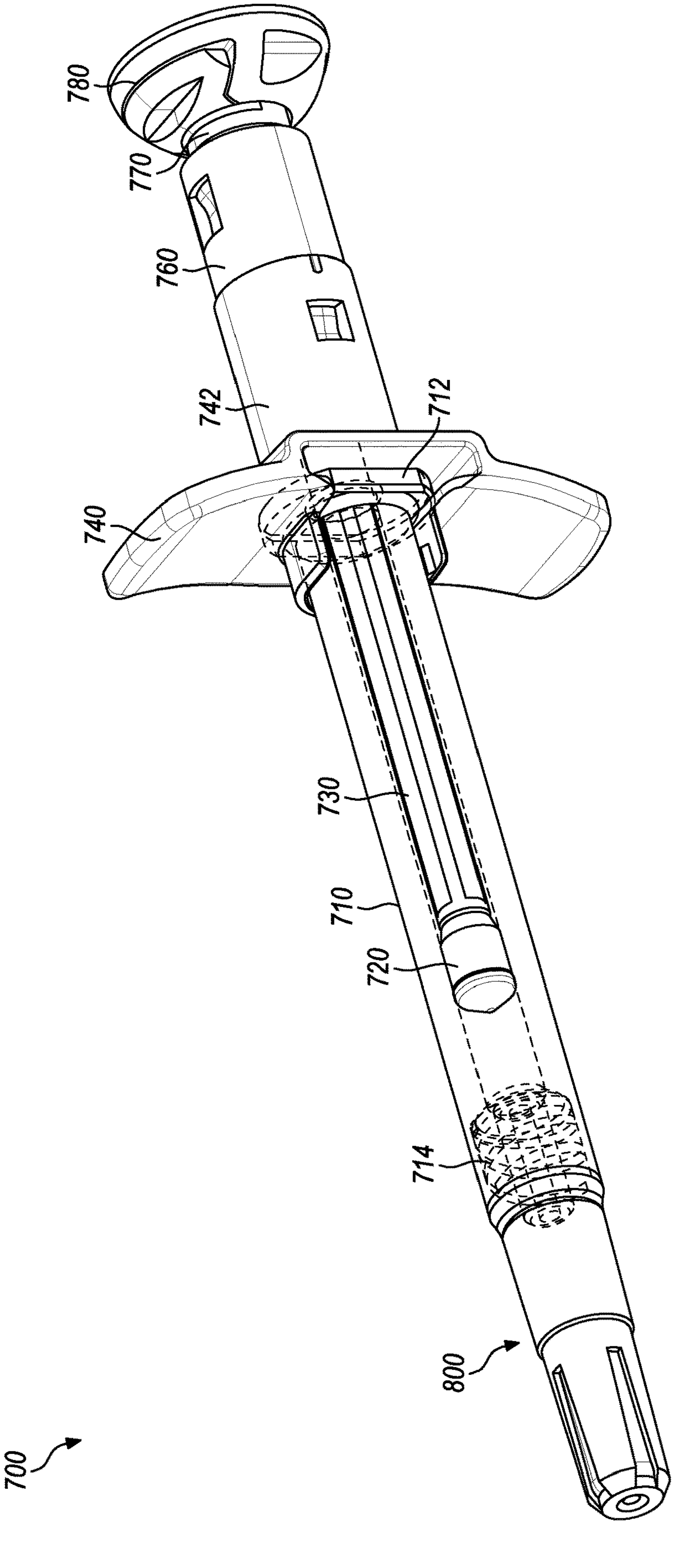
FIGS. 16 and 17 are perspective and side views of a multiple site dispensing and/or injection system with an applicator tip and a cap according to some embodiments.
Figure 17:
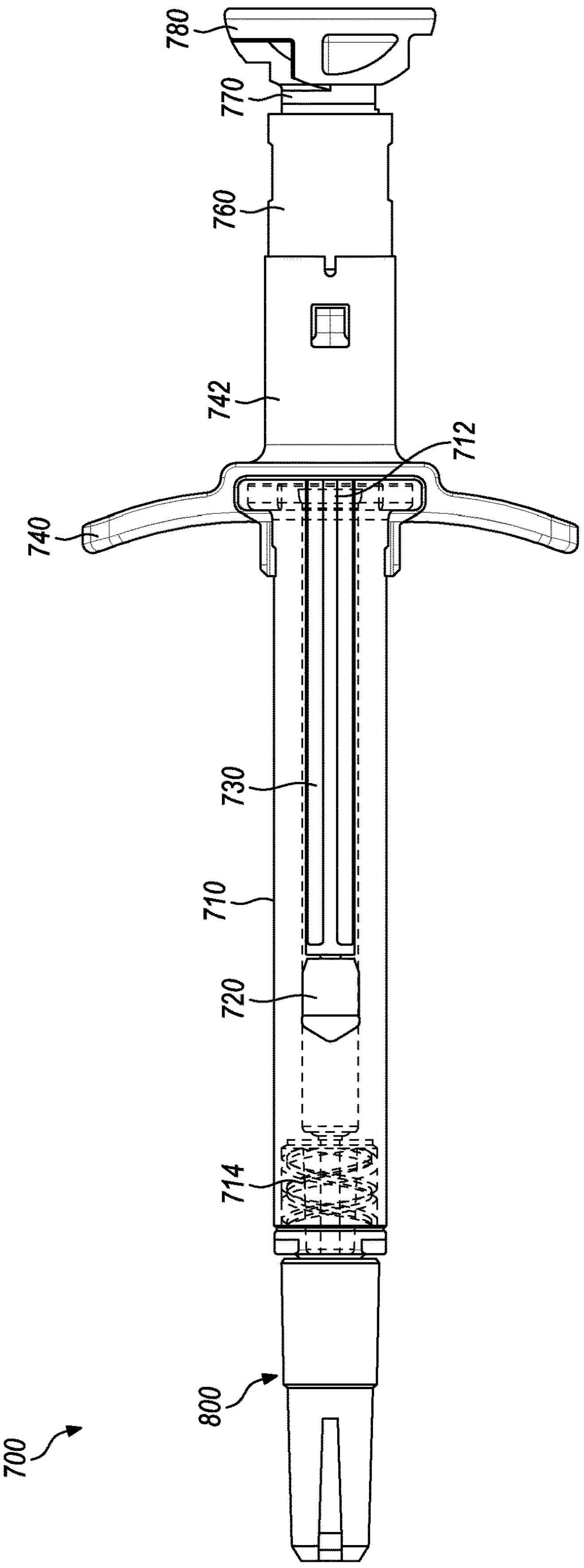

FIGS. 16 and 17 are perspective and side views of a multiple site dispensing system 700 with an applicator tip (see FIGS. 19 and 20) and a cap 800 according to some embodiments. The multiple site dispensing system 700 depicted in FIGS. 16 to 20 is almost identical to the multiple site dispensing and/or injection system 600 depicted in FIGS. 6 to 15. For instance, the multiple site dispensing system 700 includes a syringe body 710, a stopper member 720, a plunger member 730, and a finger flange 740. The syringe body 710 includes a syringe flange 712 at a proximal end thereof on which the finger flange 740 is coupled. The syringe body 710 also includes a needle hub coupling member 714. The only difference between the two systems 600, 700 is that system 700 includes an applicator tip (see FIGS. 19 and 20) and a cap 800. Aspects of the multiple site dispensing system 700 similar to aspects of the multiple site dispensing and/or injection system 600 have corresponding reference numerals that only differ in the first digit and have similar functions as the aspects of the system 600 described above.

Multiple site dispensing system 700 includes a syringe body 710 and a finger flange 740 coupled thereto. The syringe body 710 includes a syringe flange 712 at a proximal end thereof on which the finger flange 740 is coupled. The syringe body 710 also includes a coupling member 714 (e.g., a female Luer connector) and an applicator tip (see FIGS. 19 and 20) coupled thereto. A cap 800 is removably coupled to the applicator tip.

Figure 19:
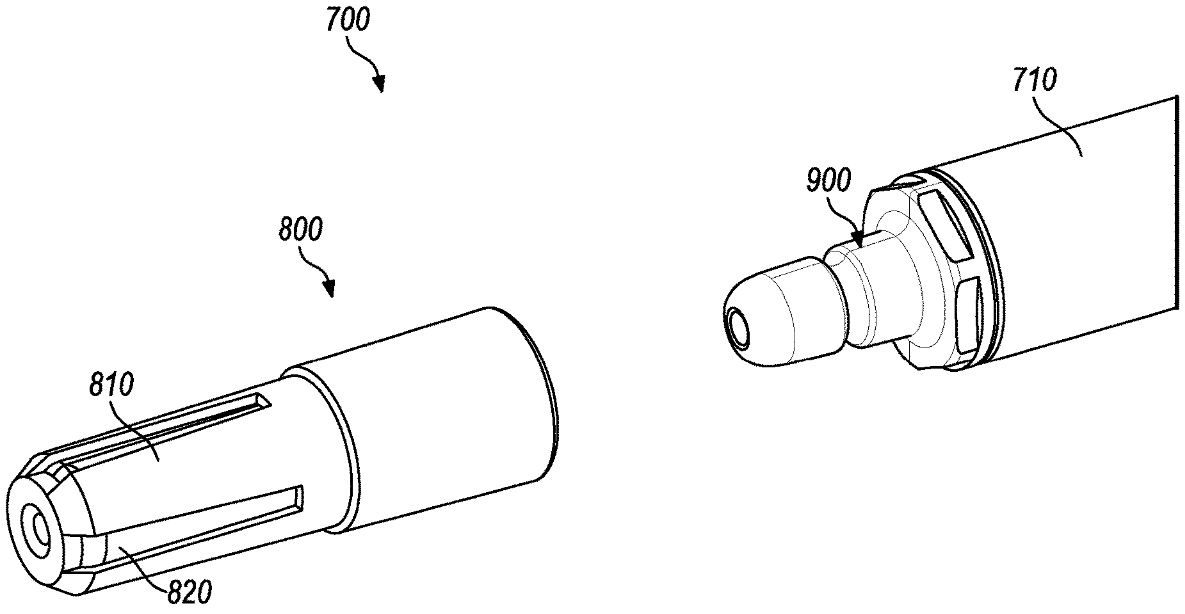
FIG. 19 is an exploded detailed perspective view of a multiple site dispensing and/or injection system with an applicator tip and a cap according to some embodiments.
Figure 20:
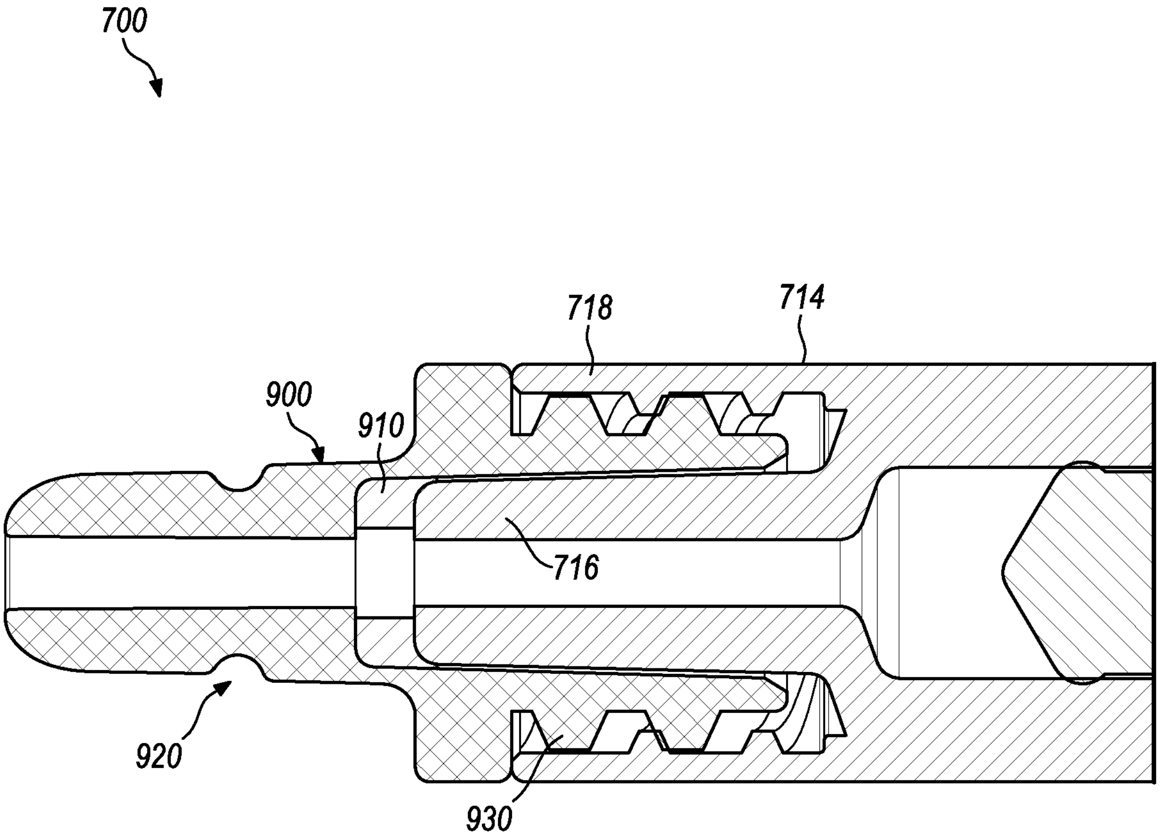
FIG. 20 is a detailed longitudinal cross-sectional view of a multiple site dispensing and/or injection system with an applicator tip and a cap according to some embodiments.

The finger flange 740 includes a proximally projecting tubular member 742. The system 700 also includes an outer telescoping member 760 formed at a proximal end of a push member (not shown). The system 700 further includes an inner telescoping member 770 slidably and at least partially disposed within the outer telescoping member 760. A thumbpad 780 is coupled to a proximal end of the inner telescoping member 770. As shown in FIGS. 19 and 20, an applicator tip/nozzle 900 is coupled to the coupling member 714 (female Luer connector) molded into the distal end of the syringe body 710, for instance with a male Luer connector. In turn, a cap 800 is removably attached to the applicator tip 900. In embodiments including connectors (e.g. Luer), the applicator tip 900 may be attached to the syringe body 710 by a user immediately prior to dispensing. In other embodiments, the applicator tip 900 is welded onto the syringe body 710 during manufacturing. The applicator tip 900 is configured to dispense a substance (e.g., liquid or gel) from a syringe body 710 multiple times.

The cap 800 may include a rigid polymer shell 810 and an elastic inner member 820 which creates a seal around an inner surface of the cap 800. When the user is ready to dispense, they may pull the cap 800 off and depress the thumbpad 780. When dispensing is complete, the user may reattach the cap 800, thereby preventing contamination and/or accidental dispensing.

Figure 18:
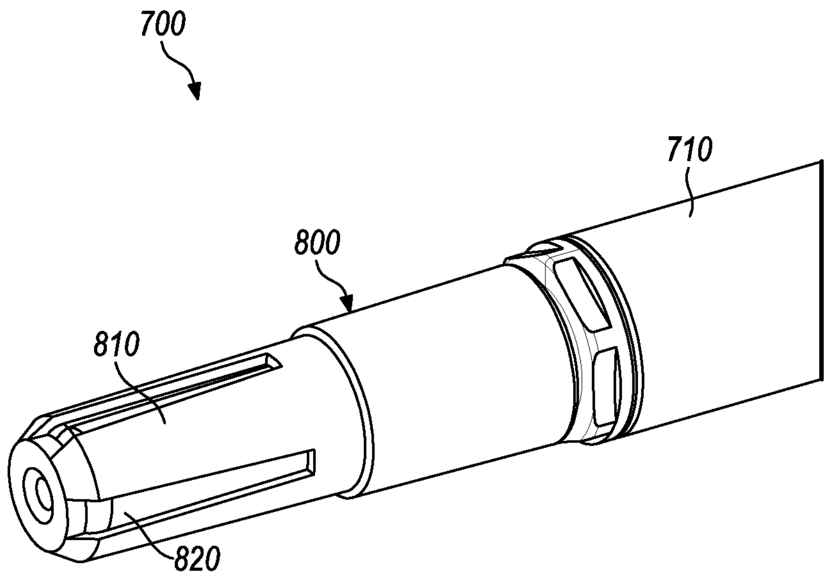
FIG. 18 is a detailed perspective view of a multiple site dispensing and/or injection system with an applicator tip and a cap according to some embodiments.

FIG. 18 is a detailed perspective view of a multiple site dispensing system with an applicator tip and a cap according to some embodiments. FIG. 19 is an exploded detailed perspective view of a multiple site dispensing system with an applicator tip and a cap according to some embodiments. FIG. 20 is a detailed longitudinal cross-sectional view of a multiple site dispensing system with an applicator tip and a cap according to some embodiments.

As shown in FIG. 20, between the applicator tip 900 and the Luer cone 716 of the coupling member 714 of the syringe body 710 there is an elastic seal 910 that is lightly compressed during assembly. The seal 910 prevents fluid from leaking into the threaded region of the coupling member 714 of the syringe body 710 without relying on a compression fit between the concentric cones of the coupling member 714 of the syringe body 710 and cap 800. The applicator tip 900 defines a recessed ring 920 that facilitates removable coupling of the cap 800 as the elastic inner member 820 expands into the recessed ring 920. The applicator tip 900 facilitates control of the diameter of the cylinder of a thicker fluid (medicine) that is extruded to increase the length of the extrusion. The applicator tip 900 also includes a connector 930 (e.g., a male Luer connector) that disposed in the gap between the Luer cone 716 and a threaded collar 718 of the syringe body 710, thereby minimizing disposed fluid/medicine from being lost in this gap.

Multiple Site Injection System

Figure 21:
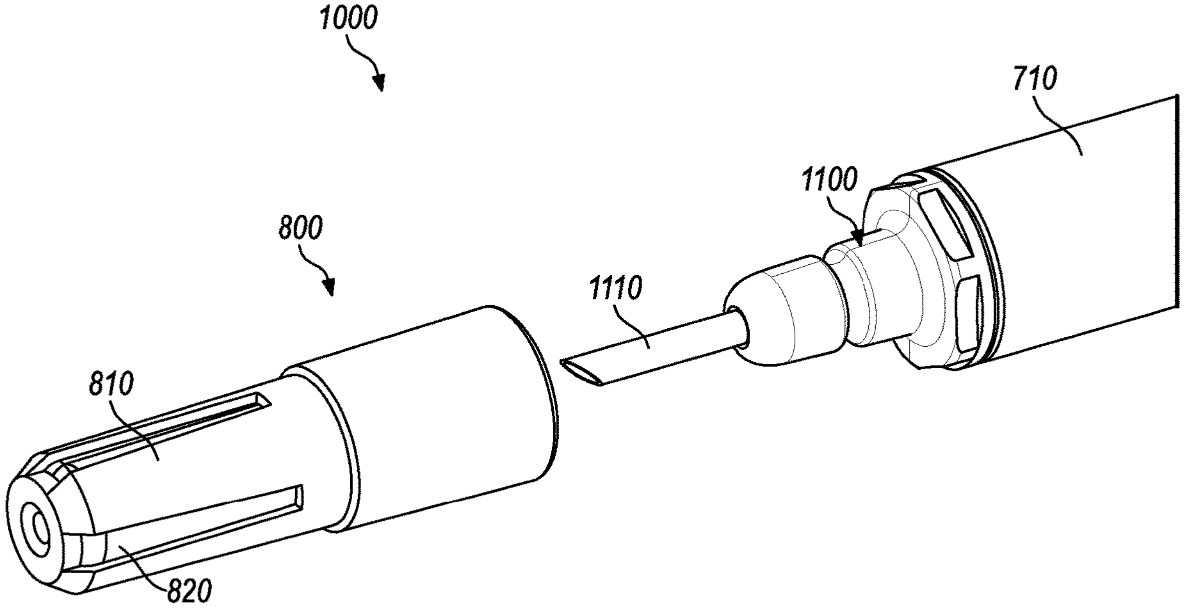
FIG. 21 is an exploded detailed perspective view of a multiple site injection system with a needle hub and a cap according to some embodiments.
Figure 22:
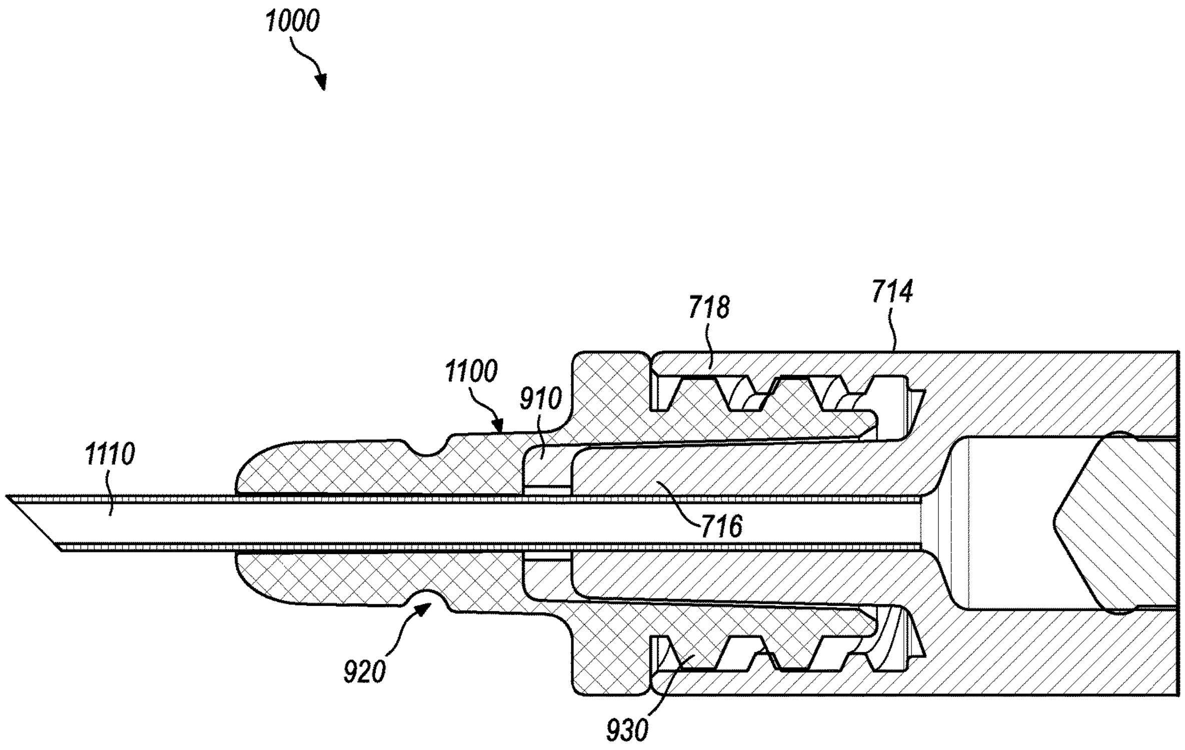
FIG. 22 is a detailed longitudinal cross-sectional view of a multiple site injection system with a needle hub and a cap according to some embodiments.

FIG. 21 is an exploded detailed perspective view of a multiple site injection system 1000 with a needle hub 1100 and a cap 800 according to some embodiments. FIG. 22 is a detailed longitudinal cross-sectional view of a multiple site injection system 1000 with a needle hub 1100 and a cap 800 according to some embodiments.

The multiple site injection system 1000 depicted in FIGS. 21 to 22 is almost identical to the multiple site dispensing and/or injection system 600 depicted in FIGS. 6 to 15 and the multiple site dispensing system 700 depicted in FIGS. 16-20. The only difference between these systems 600, 700, 1000 is that system 1000 includes a needle hub 1100. Aspects of the multiple site injection system 1000 similar to aspects of the multiple site dispensing and/or injection systems 600, 700 have corresponding reference numerals that only differ in the first digit and have similar functions as the aspects of the system 600 described above. The needle hub 1100 includes a needle 1110 configured to inject a substance (e.g., liquid or gel) from a syringe body 710 multiple times into a patient.

While the dispensing and/or injection systems depicted and described herein include syringes with Luer connectors, the multiple site dispensing and/or injection systems described herein can be used with staked needles, cartridges, and auto injectors, etc. The multiple site dispensing and/or injection systems described herein can also be used with safe dispensing and/or injection systems such as those described in U.S. patent application Ser. No. 14/696,342, the contents of which have been previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for fluid delivery, comprising:

a syringe body having proximal and distal ends, a syringe interior, and a syringe flange at the proximal end thereof;

a fluid disposed in the syringe interior;

a finger flange coupled to the syringe flange;

a stopper member disposed in the syringe interior;

a plunger member coupled to the stopper member and having a ratchet portion;

a push member disposed coaxially around at least a portion of the plunger member and operatively coupled thereto, the push member having an outer telescoping member disposed at a proximal end thereof;

an inner telescoping member disposed slidably and at least partially in the outer telescoping member and operatively coupled thereto; and a thumbpad disposed coupled to a proximal end of the inner telescoping member, wherein the finger flange comprises a proximally projecting tubular member, wherein a distal end of the push member is disposed in the proximally projecting tubular member, wherein the proximally projecting tubular member of the finger flange defines a proximally facing surface, and wherein the outer telescoping member of the push member defines a distally facing surface configured to interfere with the proximally facing surface of the proximally projecting tubular member of the finger flange to limit distal movements of the push member relative to the finger flange.

2. The system of claim 1, wherein the outer telescoping member of the push member defines a side opening having a proximally facing wall, and wherein the inner telescoping member defines a distally tapering member configured to interfere with the proximally facing wall of the side opening of the outer telescoping member of the push member to limit distal movement of the inner telescoping member relative to the outer telescoping member of the push member.

3. The system of claim 2, further comprising a distal spring disposed in the proximally projecting tubular member of the finger flange and between and in contact with the finger flange and the push member.

4. The system of claim 3, further comprising a proximal spring disposed in the outer telescoping member of the push member between and in contact with the push member and the inner telescoping member.

5. The system of claim 4, wherein the distal spring is weaker than the proximal spring, with less pre-load in a resting state, such that applying a distally directed force to the inner telescoping member through the thumbpad initially compresses the distal spring until the distally facing surface of the push member abuts the proximally facing surface of the proximally projecting tubular member of the finger flange before compressing the proximal spring to allow the inner telescoping member to move distally relative to the outer telescoping member.

6. The system of claim 4, wherein the distal spring is stronger than the proximal spring, with more pre-load in a resting state, such that applying a distally directed force to the inner telescoping member through the thumbpad initially compresses the proximal spring until the distally tapering member of the inner telescoping member abuts the proximally facing wall of the outer telescoping member of the push member before compressing the distal spring to allow the push member to move distally relative to the finger flange.

7. The system of claim 4, wherein the distal spring and proximal spring have equal strength, such that the push member and the inner telescoping member move simultaneously.

8. The system of claim 1, wherein the push member comprises a distally extending pawl in contact with and operatively coupled to the ratchet portion of the plunger member.

9. The system of claim 8, wherein the ratchet portion of the plunger member comprises a plurality of teeth.

10. The system of claim 9, wherein a full depression of the thumbpad relative to the finger flange advances the plunger member distally relative to the syringe body by a distance of one tooth of the plurality of teeth.

* * * * *